US010340036B2

(12) United States Patent
Takahashi et al.

(10) Patent No.: US 10,340,036 B2
(45) Date of Patent: Jul. 2, 2019

(54) DATA MANAGEMENT MECHANISM FOR WIDE-AREA DISTRIBUTED MEDICAL INFORMATION NETWORK

(71) Applicant: INTERNATIONAL BUSINESS MACHINES CORPORATION, Armonk, NY (US)

(72) Inventors: Nobuaki Takahashi, Tokyo (JP); Gaku Yamamoto, Tokyo (JP)

(73) Assignee: International Business Machines Corporation, Armonk, NY (US)

( * ) Notice: Subject to any disclaimer, the term of this patent is extended or adjusted under 35 U.S.C. 154(b) by 175 days.

(21) Appl. No.: 14/081,410

(22) Filed: Nov. 15, 2013

(65) Prior Publication Data
US 2014/0156305 A1 Jun. 5, 2014

(30) Foreign Application Priority Data
Nov. 30, 2012 (JP) .................................. 2012-262779

(51) Int. Cl.
*G16H 10/60* (2018.01)
(52) U.S. Cl.
CPC .................................. *G16H 10/60* (2018.01)
(58) Field of Classification Search
CPC ....................... G06F 11/1464; G06F 17/30867; G16H 10/60
USPC ................................... 705/2; 726/8; 718/101
See application file for complete search history.

(56) References Cited

U.S. PATENT DOCUMENTS

| 5,916,307 A * | 6/1999 | Piskiel .................... G06F 9/546 718/101 |
| 2002/0007284 A1* | 1/2002 | Schurenberg .......... G06Q 10/10 705/2 |
| 2002/0079203 A1* | 6/2002 | Kikuta ................... B60Q 5/003 200/61.54 |

(Continued)

FOREIGN PATENT DOCUMENTS

| JP | 10-079770 | 3/1998 |
| JP | 2001-350847 | 12/2001 |

(Continued)

OTHER PUBLICATIONS

"How Database Mirroring Works"; Microsoft SQL Server website; 2008.*

(Continued)

*Primary Examiner* — John A Pauls
(74) *Attorney, Agent, or Firm* — Law Office of Jim Boice

(57) ABSTRACT

A method distributes and manages medical information on a communication network over a wide area. Encrypted medical information is acquired from one of a plurality of first computers by a second computer connected to the communication network, the plurality of first computers being connected to the communication network, holding identical medical information, encrypting medical information, and sending and receiving encrypted medical information. The second computer decrypts the acquired encrypted medical information, browses and updates decrypted medical information, and then encrypts the browsed and updated medical information. The second computer then sends the encrypted browsed and updated medical information to the plurality of first computers.

13 Claims, 7 Drawing Sheets

(56) References Cited

U.S. PATENT DOCUMENTS

| | | | | |
|---|---|---|---|---|
| 2002/0103917 A1* | 8/2002 | Kay | ............... | G06F 17/30867 |
| | | | | 709/229 |
| 2004/0078229 A1* | 4/2004 | Gay | ............... | G06Q 50/22 |
| | | | | 705/2 |
| 2005/0010760 A1 | 1/2005 | Goh et al. | | |
| 2007/0271316 A1* | 11/2007 | Hollebeek | ............... | G06F 11/1464 |
| 2009/0221363 A1* | 9/2009 | Brunet de Courssou | ............... | |
| | | | | G07F 17/32 |
| | | | | 463/25 |
| 2010/0031335 A1* | 2/2010 | Handler | ............... | H04L 9/3226 |
| | | | | 726/8 |
| 2010/0115609 A1 | 5/2010 | Spence | | |
| 2013/0006867 A1 | 1/2013 | Dove et al. | | |
| 2014/0156988 A1 | 6/2014 | Takahashi et al. | | |

FOREIGN PATENT DOCUMENTS

| | | |
|---|---|---|
| JP | 2003-196386 | 7/2003 |
| JP | 2004-030128 | 1/2004 |
| JP | 2004341961 A | 12/2004 |
| JP | 2005-025669 | 1/2005 |
| JP | 2006-246401 A | 9/2006 |
| JP | 2010-097418 | 4/2010 |
| JP | 2010165214 A | 7/2010 |
| JP | 2010-186250 | 8/2010 |
| JP | 2011-181025 | 9/2011 |
| JP | 2011-198310 | 10/2011 |

OTHER PUBLICATIONS

"Database Mirroring Sessions"; Microsoft SQL Server website; 2008.*

Synchronous Database Mirroring (High-safety Mode); Microsoft SQL Server website; 2008.*

"Database Mirroring Overview"; Microsoft SQL Server website; 2008.*

U.S. Appl. No. 14/081,496—Non-Final Office Action dated May 29, 2015.

U.S. Appl. No. 14/081,496 Final Office Action dated Nov. 24, 2015.

U.S. Appl. No. 14/081,496 Examiner's Answer dated Nov. 10, 2016.

U.S. Appl. No. 14/081,496 Decision on Appeal dated Mar. 28, 2018.

* cited by examiner

DATA MANAGEMENT MECHANISM FOR WIDE-AREA DISTRIBUTED MEDICAL INFORMATION NETWORK

This application is based on and claims the benefit of priority from Japan (JP) Patent Application 2012-262779, filed on Nov. 30, 2012, and herein incorporated by reference in its entirety.

BACKGROUND

The present invention relates to management of medical information on a communication network and, in particular, to a method, system and computer program for distributing and managing medical information distributed on a communication network over a wide area.

The importance of sharing electronic medical records among medical institutions has been recognized and such sharing has been actually implemented in some local communities and medical institutions. Standardization of the data formats of electronic medical records is being facilitated and the foundation to enable sharing electronic medical records is being laid. From a practical point of view, however, sharing of electronic records has not been widespread. This is because building a system that manages electronic medical records costs a large amount of money.

SUMMARY

In one embodiment of the present invention, a method and/or computer program product distributes and manages medical information on a communication network over a wide area. Encrypted medical information is acquired from one of a plurality of first computers by a second computer connected to the communication network, the plurality of first computers being connected to the communication network, holding identical medical information, encrypting medical information, and sending and receiving encrypted medical information. The second computer decrypts the acquired encrypted medical information, browses and updates decrypted medical information, and then encrypts the browsed and updated medical information. The second computer then sends the encrypted browsed and updated medical information to the plurality of first computers.

In one embodiment of the present invention, a system distributes and manages medical information on a communication network over a wide area. The system comprises: a plurality of first computers connected to the communication network, the plurality of first computers holding identical medical information, encrypting the medical information and sending and receiving the encrypted medical information; and a second computer connected to the communication network, the second computer comprising an acquisition section for acquiring encrypted medical information from any of the plurality of first computers, a decrypting section for decrypting the encrypted medical information acquired by the acquisition section, a browsing and updating section for browsing and updating the medical information decrypted by the decrypting section, an encryption section for encrypting the medical information browsed and updated on the browsing and updating section, and a sending section for sending the browsed and updated medical information encrypted by the encryption section to the plurality of first computers.

DETAILED DESCRIPTION

Figure 1:
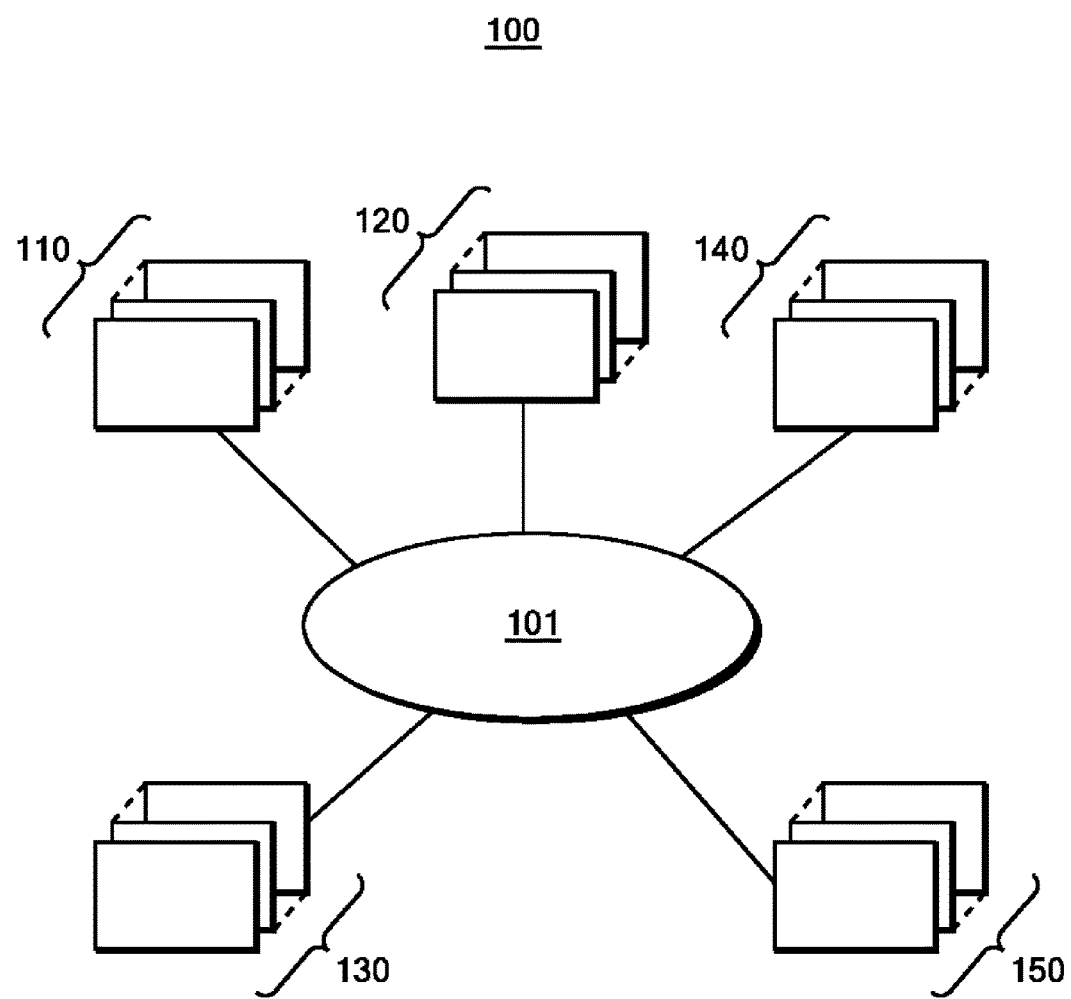
FIG. 1 is a schematic diagram of a configuration of a wide-area distributed medical information network system 100 according to an embodiment of the present invention.

The best mode for carrying out the present invention will be described below in detail with respect to drawings. However, the embodiment described below is not intended to limit the present invention which is defined in the claims and not all combinations of features described in the embodiment are essential to the inventive solution. The present invention can be carried out in many different modes and should not be interpreted as being limited to the specifics in the descriptions of the embodiment. Throughout the description of the embodiment, like components or elements are given like reference numerals.

FIG. 1 schematically illustrates a configuration of a wide-area distributed medical information network system 100 according to one embodiment of the present invention. The network system 100 includes one or more medical data management computers 110 and one or more medical data management replica computers 120, which correspond to a first computer, one or more medical data address management computer 130, which corresponds to a third computer, one or more medical data temporary storage computers 140, which correspond to a fourth computer, and one or more medical data browsing and updating computers 150 which correspond to a second computer, all of which are connected to a communication network 101 such as the Internet.

This is a master computer that stores patients' medical data, such as electronic medical records. The medical data management computer 110 stores encrypted medical data along with identification information (ID) of patients. For a plurality of patients, a plurality of pieces of identification information and encrypted medical data are stored. The medical data management computer 110 includes the function of encrypting medical data of interest and sending the encrypted medical data in response to a reference request from an external requester by externally accessing with identification information of a patient and the function of receiving updated encrypted medical data, decrypting and storing the data in response to an update request from an external requester. The medical data management computer 110 also includes the function of combining updated portions of data held in a plurality of update requests to generate up-to-data medical data when the medical data management computer 110 receives the plurality of update requests. Furthermore, the medical data management computer 110 provides updated latest medical data to a medical data management replica computer 120. Medical data has medical data address information, which includes identification information of a patient and address information of the computer that manages the medical data, for example the medical data management computer 110 or the medical data management replica computer 120. Encrypted medical data can be decrypted by a person who has key information such as a secrete key for decrypting the encrypted medical data, such as a person concerned, for example the patient, and can be accessed and updated by the person concerned. The medical data management computer 110 may be a personal computer at the home of a patient themselves, a server computer at a medical institution, or a server computer of a service provider that provides medical data management services.

The medical data management replica computer 120 includes the function of holding replicas, that is, copies, of patients' medical data stored in the medical data management computer 110 and sending medical data of interest in response to a reference request from an external requester, and the function of receiving and storing updated medical data in response to an update request from an external requester. The medical data management replica computer 120 may be a personal computer at the home of a relative or a friend of a patient, a server computer at a medical institution, or a server computer of a service provider that provides medical data management services.

The medical data address management computer 130 holds address information of medical data management computers 110 and medical data management replica computers 120 on which medical data of patients identified by identification information of the patients are stored. The medical data address management computer 130 has the function of recording identification information of a patient and address information of the medical data management computer 110 and the medical data management replica computer 120 when receiving an address registration request from an external requester. The medical data address management computer 130 also holds address information of another medical data address management computer 130. The medical data address management computer 130 has the function of returning address information of the medical data management computer 110 or medical data management replica computer 120 identified by identification information of a patient specified in an address request in response to the address request from an external requester. The medical data address management computer 130 has the function of, if there is not address information of a patient specified in a request, sending a request for address information of a computer that manages medical data to another medical data address management computer 130 using held address information along with the identification information of the patient and returning the acquired address information of the computer that manages the medical data to the requester. Patients or other parties can register address information of the medical data management computer 110 and the medical data management replica computer 120 that store medical data in a plurality of medical data address management computers 130 so that address information thus registered can be efficiently acquired. The computer may be a server computer at a medical institution or a server computer of a service provider providing medical data management services, for example.

Medical Data Temporary Storage Computer 140 is a computer temporarily storing updated medical data. When receiving updated encrypted medical data and data about the medical data management computer 110 or the medical data management replica computer 120 that stores the medical data from an external source, the medical data temporary storage computer 140 temporarily stores the data. For encrypted medical data stored in the medical data temporary storage computer 140, the medical data temporary storage computer 140 sends a medical data update request to a relevant medical data management computer 110 or a relevant medical data management replica computer 120 at regular intervals. The temporarily stored encrypted medical data is held until all of the medical data management computers 110 or medical data management replica computers 120 to which the data has been sent complete reception of the medical data. The computer may be a server computer of a medical institution or a server computer of a service provider providing medical data management services, for example.

Medical Data Browsing and Updating Computer 150 is a computer for browsing and updating (browsing or updating) medical data, for example a computer used by a doctor. The medical data browsing and updating computer 150 is configured to be able to send a request for address information of a computer that manages medical data to one or medical data address management computers 130 along with identification information of a patient. When a user (for example a doctor or a nurse) inputs identification information of a patient, the medical data browsing and updating computer 150 acquires address information of the medical data management computer 110 or medical data management replica computer 120 that manages medical data of that patient from a medical data address management computer 130 and sends a medical data request to a relevant one of the computers. When receiving encrypted medical data as a reply to the sent request, the user inputs key information, for example, that constitutes decryption information for decrypting the encrypted medical data to decrypt the encrypted medical data. Here, the key information for decryption may be a personal identification number or a password, for example, which may be recorded on an IC card or the like in some cases. When the user has updated medical data, the user inputs key information, for example, that constitutes encryption information for encrypting the medical data to encrypt the medical data and sends the encrypted medical data to the medical data management computer 110 or the medial data management replica computer 120 or a medical data temporary storage computer 140 in association with the identification information of the patient. The medial data browsing and updating computer 150 may be a terminal computer used by a doctor or a nurse at a medical institution, for example.

Here, since medical data management computers 110 and medical data management replica computers 120 can be personal computers of individuals, they are not necessarily operating all the time. Furthermore, these computers do not necessarily physically different computers. For example, a large medical institution may run the functional modules of the medical data management computer 110 and the functional modules of the medical data address management computer 130 on the same computer. However, in order to protect medical records from the risk of a disaster, these computers are preferably configured with physically different computers and distributed in locations remote from each other.

Since medical data management computers 110 and the medical data management replica computers 120 may be personal computers of individuals and are not necessarily operating all the time, medical data of one patient is stored on a plurality of medical data management computers 110 and medical data management replica computers 120 in the wide-area distributed medical information network system 100. Let N denote the number of those computers, then all of the N computers are not necessarily operating all the time. Even in such a situation, the wide-area distributed medical information network system 100 can perform distributed management of medical information. This will be described below.

Figure 2:
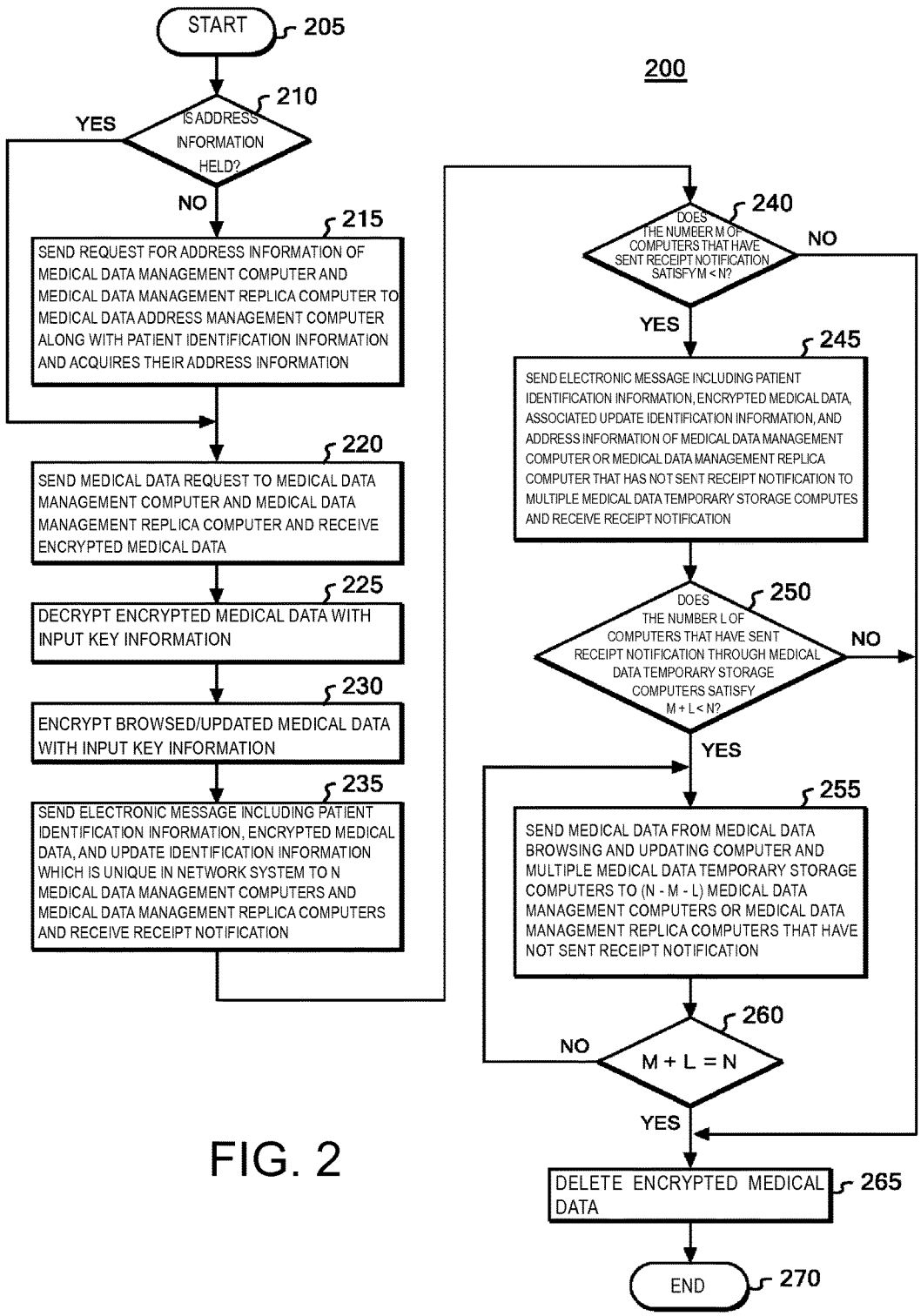
FIG. 2 is a schematic flowchart of a process performed by a medical data browsing and updating computer 150.

FIG. 2 illustrates a general flow 200 of a process performed by a medical data browsing and updating computer 150. As has been described previously, a user, for example a doctor or a nurse, acquires identification information of a patient from the patient and inputs the identification information in the medical data browsing and updating computer 150 to start the process (step 205). The medical data browsing and updating computer 150 determines whether or not the medical data browsing and updating computer 150 holds address information of a medical data management computer 110 and a medical data management replica computer 120 that manage medical data of the patient (step 210). If the medical data browsing and updating computer 150 does not hold the address information (NO), the medical data browsing and updating computer 150 sends a request for the address information of the medical data management computer 110 and the medical data management replica computer 120 that manage the medical data of the patients to one or more medical data address management computers 130 connected through a communication network 101 along with the identification information of the patient and acquires the address information of the computers (step 215). After the medical data browsing and updating computer 150 has acquired the address information or if the medical data browsing and updating computer 150 determines at step 210 that it holds the address information (YES), the medical data browsing and updating computer 150 sends a medical data request to the medical data management computer 110 and the medical data management replica computer 120 that are connected through the communication network 101 and are identified by the address information and receives encrypted medical data (step 220). When the user acquires key information, for example, which constitutes decryption information for decrypting the encrypted medical data from the patient or other party and inputs the key information in the medical data browsing and updating computer 150, the medical data browsing and updating computer 150 decrypts the encrypted medical data with the key information (step 225). When the user browses and/or updates the medical data and then inputs key information, for example, which constitutes encryption information for encrypting the medical data in the medical data browsing and updating computer 150, the medical data browsing and updating computer 150 encrypts the browsed/updated medical data with the key information (step S230).

Figure 3:
FIG. 3 is a schematic diagram of a structure of an electronic message sent from a medical data browsing and updating computer 150 and a medical data temporary storage computer 140 to a medical data management computer 110 and a medical data management replica computer 120.

The medical data browsing and updating computer 150 sends an electronic message 300 as illustrated in FIG. 3 that includes the identification information of the patient, the encrypted medical data, and update identification information that is unique in the wide-area distributed medical information network system 100 to the N medical data management computers 110 and medical data management replica computers 120 and receives a receipt notification from the medical data management computers 110 and the medical data management replica computers 120 (step 235). The update identification information may be implemented by information including an IP address, for example, of the medical data browsing and updating computer 150 and update time data.

Figure 4:
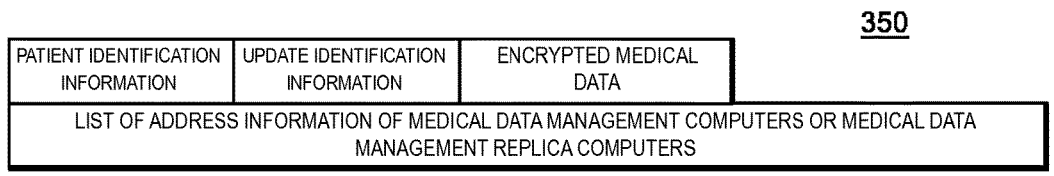
FIG. 4 is a schematic diagram of a structure of an electronic message sent from a medical data browsing and updating computer 150 to a medical data temporary storage computer 140.

The medical data browsing and updating computer 150 determines whether or not the number M of the medical data management computers 110 and the medical data management replica computers 120 that have sent a notification of receipt of the electronic message satisfies M<N (step 240). If M<N (YES), the medical data browsing and updating computer 150 sends an electronic message 350 as illustrated in FIG. 4 that includes the identification information of the patient, the encrypted medical data, and the associated update identification information, and the address information of the medical data management computers 110 or medical data management replica computers 120 that have not sent a receipt notification to (N−M) or more medical data temporary storage computers 140, if (N−M) or more computers connected through the communication network 101 are available, and receives a receipt notification from medical data management computers 110 and medical data management replica computers 120 through a plurality of medical data temporary storage computers 140 (step 245). The medical data browsing and updating computer 150 has acquired address information of the plurality of medical data temporary storage computers 140 connected through the communication network 101 in advance so that the medical data browsing and updating computer 150 can use those medical data temporary storage computers 140.

The medical data browsing and updating computer 150 determines whether or not the number L of the medical data management computers 110 and the medical data management replica computers 120 that have sent a notification of receipt of the sent electronic message through the plurality of medical data temporary storage computers 140 satisfies M+L<N (step 250). If M+L<N (YES), the medical data browsing and updating computer 150 sends the medical data in an electronic message 300 as illustrated in FIG. 3 to the (N−M−L) medical data management computers 110 or medication data management replica computers 120 that have not sent a receipt notification and sends the medical data in an electronic message 350 as illustrated in FIG. 4 to a plurality of medical data temporary storage computers 140 to cause the medical data temporary storage computers 140 to send the medical data (step 255), and determines whether or not the numbers M and L of the medical data management computers 110 and the medical data management replica computers 120 that have sent a notification of receipt of the medical data sent from the medical data browsing and updating computer 150 and the medical data temporary storage computers 140, respectively, are M+L=N (step 260). If not M+L=N (NO), the process returns to step 255 and the medical data browsing and updating computer 150 and the medical data temporary storage computers 140 repeat sending the medical data to medical data management computers 110 or medical data management replica computers 120 that have not sent a receipt notification.

Since sending of browsed and updated medical data to the medical data management computers 110 and the medical data management replica computers 120 is performed by the medical data temporary storage computers 140 as well as the medical data browsing and updating computers 150, the medical data management computers 110 and the medical data management replica computers 120 may receive browsed and updated medical data duplicately. In the wide-area distributed medical information network system 100, the medical data management computers 110 and the medical data management replica computers 120 address duplicate reception of medical data by performing the following process.

The medical data management computers 110 and the medical data management replica computers 120 refer to the update identification information in a received electronic message to determine whether or not the received electronic message includes the same update identification information that is included in an electronic message they have already received and, if the medical data management computers 110 and the medical data management replica computers 120 determine that the electronic message includes different update identification information, store the encrypted medical data and the update identification information included in the received electronic message and send a receipt notification to the computer that has sent the electronic message; if the medical data management computers 110 and the medical data management replica computers 120 determine that the electronic message includes the same update identification information, they send a duplicate-receipt notification to the computer that has sent the electronic message. Because of this capability, when the medical data management computers 110 and the medical data management replica computers 120 duplicately (i.e., repeatedly) receive browsed and updated medical data, the medical data management computers 110 and the medical data management replica computers 120 return a duplicate-receipt notification, instead of a receipt notification, to the computer that has sent the electronic message. When a medical data management computer 110 or a medical data management replica computer 120 receives an electronic message first from a medical data temporary storage computer 140 and then receives an electronic message from a medical data browsing and updating computer 150 or an electronic message from another medical data temporary storage computer 140, the computer that has sent the electronic message and to which a duplicate-receipt notification is returned is that medical data browsing and updating computer 150 or that medical data temporary storage computer 140.

M medical data management computers 110 and medical data management replica computers 120 that have sent a notification of receipt of an electronic message sent from a medical data browsing and updating computer 150 and L medical data management computers 110 and medical data management replica computers 120 that have sent a notification of receipt of an electronic messages sent through a plurality of medical data temporary storage computer 140 do not include medical data management computers 110 and medical data management replica computers 120 that have sent a duplicate-receipt notification because a duplicate-receipt notification differs from a receipt notification and a receipt notification has been always sent before a duplicate-receipt notification is sent.

If the determination at step 240 is not M<N (NO), that is, if all of the medical data management computers 110 and medical data management replica computers 120 have sent a notification of receipt of an electronic message sent from a medical data browsing and updating computer 150, namely M=N, or if the determination at step 250 is not M+L<N (NO) or the determination at step 260 is M+L=N (YES), that is, all of the medical data management computers 110 and medical data management replica computers 120 have sent a notification of receipt of an electronic message from a medical data browsing and updating computer 150 and medical data temporary storage computes 140, namely M=N, the browsed and updated medical data is stored in the medical data management computers 110 and the medical data management replica computers 120 that are distributed over a wide area and connected through the communication network 101 and therefore the medical data browsing and updating computer 150 deletes the encrypted medical data (step 265) and ends the process (step 270).

Figure 5:
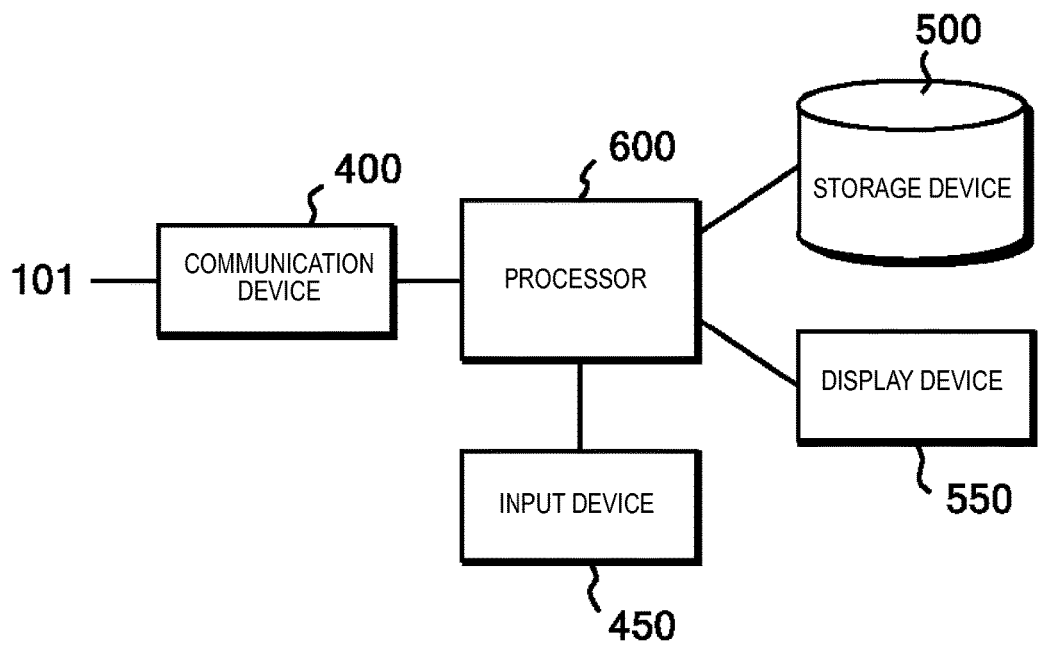
FIG. 5 is a schematic diagram illustrating a basic hardware configuration of a medical data browsing and updating computer 150 and a medical data temporary storage computer 140.

A basic hardware configuration of a medical data browsing and updating computer 150 is schematically illustrated in FIG. 5. The medical data browsing and updating computer 150 includes, a communication device 400 such as a communication adapter, for example, an input device 450 such as a keyboard and a mouse, for example, a storage device 500 such as a hard disk drive, a solid state drive and an optical drive, for example, a display device 550 such as a liquid-crystal display, for example, and a processor 600 such as a central processing unit (CPU), for example. The communication device 400 is connected to the communication network 101 and the processor 600 and is used for sending and receiving data to and from medical data management computers 110, medical data management replica computers 120, medical data address management computers 130, and medical data temporary storage computers 140. The input device 450 is connected to the processor 600 and is used for inputting medical data, identification information of patients, key information, and other data. The storage device 500 is connected to the processor 600 and is used for storing medical data, identification information of patients, update identification information, address information of the medical data management computers 110 and the medical data management replica computers 120, and other data. The display device 550 is connected to the processor 600 and is used for displaying medical data, identification information of patients, update identification information, and other information. The processor 600 is used for sending and receiving data to and from these devices 400, 450, 500 and 550 and processing data and is also used for implementing the function of distributing and storing medical data over a wide area.

Figure 6:
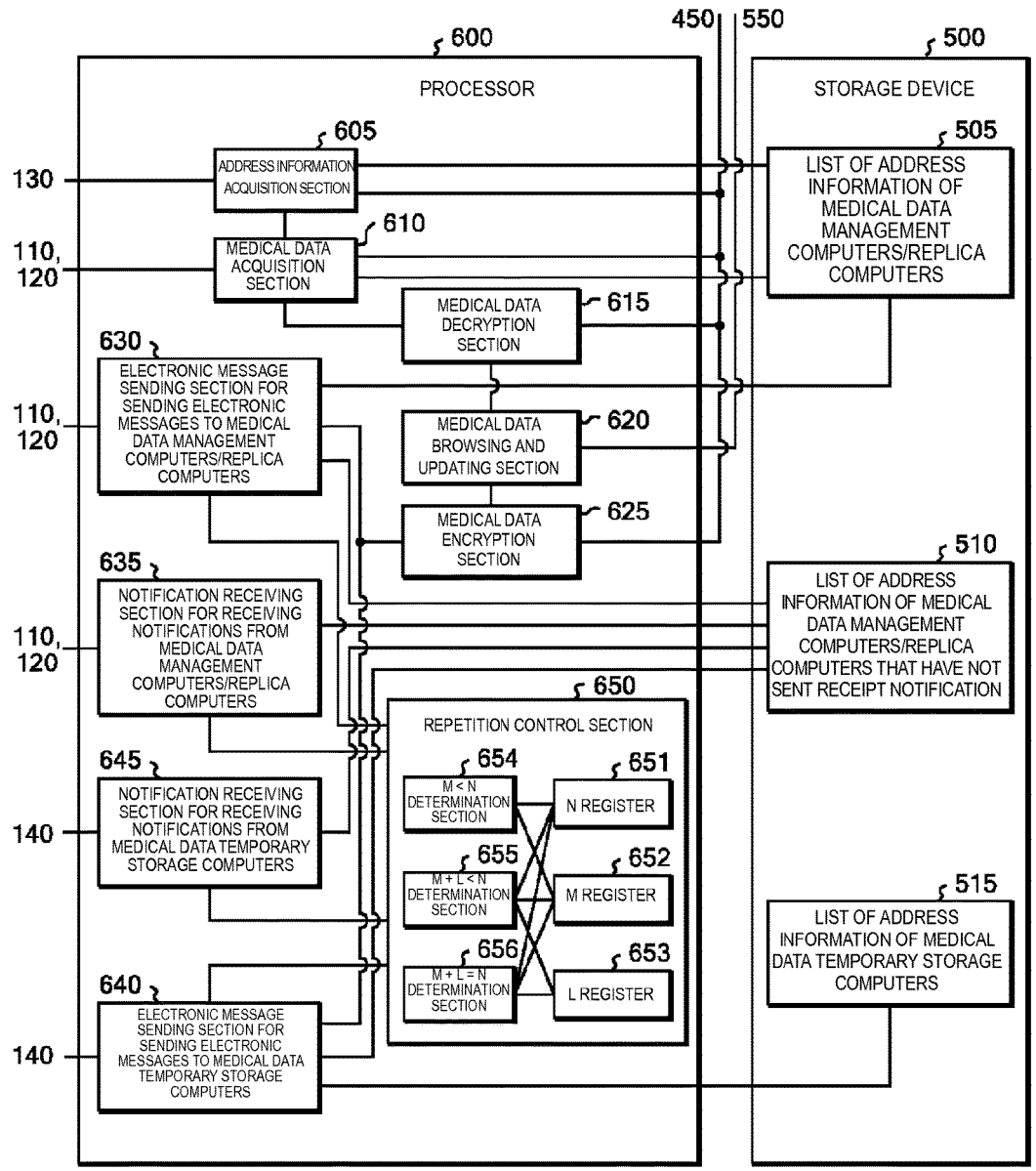
FIG. 6 is a schematic functional block diagram of a medical data browsing and updating computer 150.

FIG. 6 illustrates a configuration used for implementing the functions of the processor 600 on the medical data browsing and updating computer 150 to distribute and store medical data over a wide area. The processor 600 includes an address information acquisition section 605, a medical data acquisition section 610, a medical data decryption section 615, a medical data browsing and updating section 620, a medical data encryption section 625, an electronic message sending section 630 for sending electronic messages to medical data management computers/replica computers, a notification receiving section 635 for receiving notifications from the medical data management computers/replica computers, an electronic message sending section 640 for sending electronic messages to medical data temporary storage computers, a notification receiving section 645 for receiving notifications from the medical data temporary storage computers, and a repetition control section 650, all of which can be implemented by computer programs or micro codes. For this configuration of the processor 600, storage areas are provided in the storage device 500 for storing a list 505 of address information of the medical data management computers/replica computers, a list 510 of address information of medical data management computers/replica computers that have not sent a receipt notification, and a list 515 of address information of the medical data temporary storage computers.

When identification information of a patient is input from the input device 450, the address information acquisition section 605 refers to the address information list 505 of the medical data management computers/replica computers in the storage device 500 to determine whether or not the address information of a medical data management computer 110 and a medical data management replica computer 120 that manage the medical data of the patient is held. If the address information is not held, the address information acquisition section 605 sends a request for the address information of a medical data management computer 110 and a medical data management replica computer 120 that manage the medical data of the patient to one or more medical data address management computers 130 connected through the communication network 101 along with the identification information of the patient and acquires the address information of the computers. The address information acquisition section 605 indicates the acquired address information to the medical data acquisition section 610 and stores the acquired address information on the list 505 of address information of the medical data management computers/replica computers in the storage device 500. If the address information is held, the address information acquisition section 605 notifies the medical data acquisition section 610 that the address information of the patient is on the list 505 of address information of the medical data management computers/replica computers.

If the address information is not held, the medical data acquisition section 610 is provided with the address information from the address information acquisition section 605 after the address information acquisition section 605 acquires the address information from a medical data address management computer 130; if the address information is held, the medical data acquisition section 610 is provided with the address information from the list 505 of address information of the medical data management computers/replica computers after being notified by the address information acquisition section 605. The medical data acquisition section 610 uses the provided address information to send a medical data request to the medical data management computer 110 and the medical data management replica computer 120 that are connected through the communication network 101 and identified by the address information and receives encrypted medical data. The medical data acquisition section 610 provides the received encrypted medical data to the medical data decryption section 615.

When key information, for example, which constitutes decryption information for decrypting encrypted medical data is input from the input device 450, the medical data decryption section 615 decrypts encrypted medical data provided from the medical data acquisition section 610 with the key information and provides the decrypted medical data to the medical data browsing and updating section 620.

The medical data browsing and updating section 620 performs processes for browsing and updating medical data. For example, the medical data browsing and updating section 620 provides decrypted medical data to the display device 550 so that a user, for example a doctor or a nurse, can browse the decrypted medical data. If the user updates the medical data he/she has browsed, the medical data browsing and updating section 620 generates update identification information such as information including the IP address, for example, of the medical data browsing and updating computer 150 and update time data and adds the update identification information to the updated medical data. The medical data browsing and updating section 620 provides the updated medical data and the update identification information to the medical data encryption section 625.

When key information, for example, which constitutes encryption information for encrypting medical data is input at the input device 450, the medical data encryption section 625 encrypts updated medical data provided from the medical data browsing and updating section 620 with the key information and provides the encrypted medical data, along with update identification information provided from the medical data browsing and updating section 620, to the electronic message sending section 630 for sending electronic messages to medical data management computers/replica computers and to the electronic message sending section 640 for sending electronic messages to medical data temporary storage computers.

The electronic message sending section 630 for sending electronic messages to medical data management computers/replica computers is provided with encrypted medical data and update identification information from the medical data encryption section 625, acquires address information of N medical data management computers 110 and medical data management replica computers 120 that manage medical data of the patient from the list 505 of address information of medical data management computers/replica computers, and sends an electronic message 300 as illustrated in FIG. 3 that includes the patient identification information, the update identification information, and the encrypted medical data to the N medical data management computers 110 and medical data management replica computers 120. N is set to a value (number) up to the number of pieces of address information (the number of computers) stored on the list 505 of address information of medical data management computers 110 and medical data management replica computers 120 that manage medical data of the patient and is provided to the electronic message sending section 630 and the repetition control section 650. Once sending the electronic message to the N medical data management computers 110 and medical data management replica computers 120, the electronic message sending section 630 is controlled by the repetition control section 650 and uses address information provided from the list 510 of address information of medical data management computers/replica computers that have not sent a receipt notification to repeatedly send the electronic message to the medical data management computers 110 and the medical data management replica computers 120 that have not sent a receipt notification.

The notification receiving section 635 for receiving notifications from medical data management computers/replica computers receives a receipt notification from M medical data management computers 110 and medical data management replica computers 120. The notification receiving section 635 is configured to compare information in a received notification with information in a predetermined receipt notification, for example, to identify whether the received notification is a receipt notification or not and count the number (M) of receipt notifications. The value of M is provided to the repetition control section 650. The address information of the medical data management computers 110 or medical data management replica computers 120 is provided to the list 510 of address information of medical data management computers/replica computers that have not sent a receipt notification and is deleted from the list. If there is a computer that has not sent a receipt notification among the N medical data management computers 110 and medical data management replica computers 120 (M<N), the difference between the address information of the N computers to which the electronic message has been sent and the address information of the M computers that has sent a receipt notification can be calculated to obtain the address information of the medical data management computers 110 and the medical data management replica computers 120 that have not sent a receipt notification. The obtained address information is provided to the list 510 of address information of medical data management computers/replica computers that have not sent a receipt notification.

When receiving a notification from the repetition control section 650 that there are computers that have not sent a receipt notification among the N medical data management computers 110 and medical data management replica computers 120 (M<N), the electronic message sending section 640 for sending electronic messages to medical data temporary storage computers retrieves the address information of medical data temporary storage computers 140 from the list 515 of address information of medical data temporary storage computers and sends an electronic message 350 as illustrated in FIG. 4 that includes the identification information of the patient, the encrypted medical data, associated update identification information, and the address information of the medical data management computers 110 or medical data management replica computers 120 that have not sent a receipt notification to a plurality of medical data temporary storage computers 140. The number of the medical data temporary storage computers 140 to which the electronic message is sent is set so that the number does not exceed the number of pieces of address information (the number of computers) on the list 515 of address information of the medical data temporary storage computers but exceeds at least the number of computers that have not sent a reception notification (N−M). Once the electronic message sending section 640 has sent the electronic message to the plurality of medical data temporary storage computers 140, the electronic message sending section 640 is controlled by the repetition control section 650 and uses address information provided from the list 515 of address information of medical data temporary storage computers to repeat transmission of the electronic message to medical data temporary storage computers 140.

The notification receiving section 645 for receiving notifications from medical data temporary storage computers receives receipt notifications that the medical data temporary storage computers 140 to which the electronic message has been sent have received from L medical data management computers 110 and medical data management replica computers 120 from the medical data temporary storage computers 140. The notification receiving section 645 does not need to identify the receipt notifications because the medical data temporary storage computers 140 can identify receipt notifications from the medical data management computers 110 and medical data management replica computers 120 as has been described previously with respect to the notification receiving section 635 for receiving notification from medical data management computers/replica computers. The notification receiving section 645 is configured to receive the address information of medical data management computers 110 or medical data management replica computers 120 and, when the computer associated with the address information have sent receipt notifications, information indicating the fact, and count the number (L) of the computers that have sent the receipt notifications. The value of L is provided to the repetition control section 650. The address information of the medical data management computers 110 or medical data management replica computers 120 associated with the information indicating the receipt notifications is provided to the list 510 of address information of medical data management computers/replica computers that have not sent receipt notifications and is deleted from the list 510.

The repetition control section 650 includes an N register 651, an M register 652, an L register 653, an M<N determination section 654, an M+L<N determination section 655, and an M+L=N determination section 656. The repetition control section 650 is provided with a predetermined value of N from the processor 600 in advance and stores the value in the N register 651. The repetition control section 650 is provided with a value of M from the notification receiving section 635 for receiving notifications from medical data management computers/replica computers and stores the value in the M register 652 and is provided with a value of L from the notification receiving section 345 for receiving notifications from medical data temporary storage computers and stores the value in the L register 653. The M<N determination section 654 retrieves values of N and M from the N register 651 and the M register 652, respectively, and compares the values to make a determination. The M<N determination section 654 is implemented by a comparator that takes inputs of values of N and M and compares the values. The M+L<N determination section 655 retrieves values of N, M and L from the N register 651, the M register 652 and the L register 653, respectively, and compares M+L with N to make a determination. The M+L<N determination section 655 may include, for example, an adder that takes inputs of values of M+L and N and adds the values together and a comparator that takes inputs of values of M+L and N and compares the values. The M+L=N determination section 656 retrieves values of N, M and L from the N register 651, the M register 652 and the L register 653, respectively, and determines whether M+L=N. The M+L=N determination section 656 may have the same configuration as M+L<N determination section 655, for example, and is configured to determine a result of comparison by the comparator (determine whether or not M+L is equal to N). The M+L<N determination section 655 may be used as the M+L=N determination section 656 as well and may be caused to function as the M+L=N determination section 656 as well. When the result of determination by the M<N determination section 654 is M<N, the repetition control section 650 provides the result of the determination to the electronic message sending section 640 for sending electronic messages to medical data temporary storage computers. When the result of determination by the M+L<N determination section 655 is M+L<N, the repetition control section 650 indicates the result of the determination to the electronic message sending section 630 for sending electronic messages to medical data management computers/replica computers and to the electronic message sending section 640 for sending electronic messages to medical data temporary storage computers and controls the electronic message sending sections 630 and 640 to repeatedly send electronic messages until the M+L=N determination section 656 determines that M+L=N.

Figure 7:
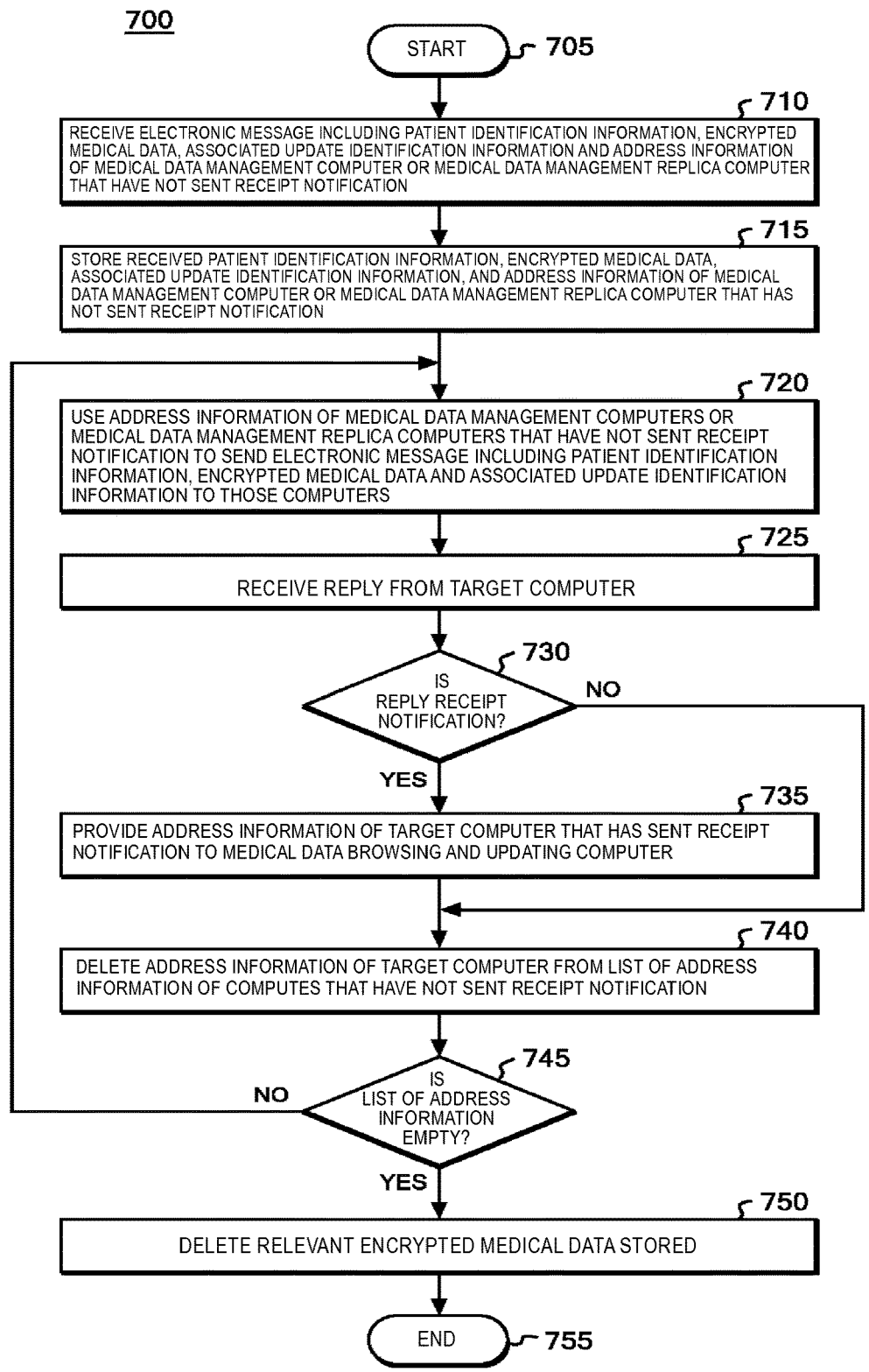
FIG. 7 is a schematic flowchart of a process performed by a medical data temporary storage computer 140.

FIG. 7 illustrates a general flow 700 of a process performed by a medical data temporary storage computer 140. As has been described previously, the medical data temporary storage computer 140 starts the process in response to an electronic message sent from a medical data browsing and updating computer 150 (step 705) and receives an electronic message 350 as illustrated in FIG. 4 that includes identification information of a patient, encrypted medical data, associated update identification information, and address information of medical data management computers 110 or medical data management replica computers 120 that have not sent a receipt notification (step 710). The medical data temporary storage computer 140 stores the identification information of the patient, the encrypted medical data, the associated update identification information, the address information of the medical data management computers 110 or medical data management replica computers 120 that have not sent a receipt notification which are included in the received electronic message (step 715). The medical data temporary storage computer 140 uses the stored address information of the medical data management computers 110 or medical data management replica computers 120 that have not sent a receipt notification to send an electronic message 300 as illustrated in FIG. 3 that includes the identification information of the patient, the encrypted medical data and the associated update identification information to those computers (step 720) and receives a reply from a medical data management computers 110 or medical data management replica computers 120 to which the electronic message 300 has been sent (step 725).

The medical data temporary storage computer 140 determines whether or not the reply is a receipt notification (step 730). If the reply is a receipt notification (YES), the medical data temporary storage computer 140 provides the address information of the medical data management computer 110 or the medical data management replica computer 120 that has sent the receipt notification to the medical data browsing and updating computer 150 along with information indicating that the receipt notification has been sent from the computer (step 735). The medical data temporary storage computer 140 deletes the address information of the computer to which the electronic message has been sent and from the stored list of address information of the medical data management computers 110 or medical data management replica computers 120 (step 740). If it is determined at step 730 that the reply is not a receipt notification (NO), the reply is a duplicate-receipt notification and therefore the medical data temporary storage computer 140 deletes the address information of the target computer to which the electronic message has been sent and from which the reply has been received from the stored list of address information of medical data management computers 110 or medical data management replica computers 120 that have not sent a receipt notification (step 740).

The medical data temporary storage computer 140 determines whether the stored list of address information of medical data management computers 110 or medical data management replica computers 120 contains no address information and is empty (step 745). If the list is not empty (NO), the medical data temporary storage computer 140 returns to step 720 and the process from step 720 through 745 is repeated. If it is determined at step 745 that the list of address information is empty (YES), the medical data temporary storage computer 140 deletes relevant stored encrypted medical data (step 750) and ends the process (step 755).

Figure 8:
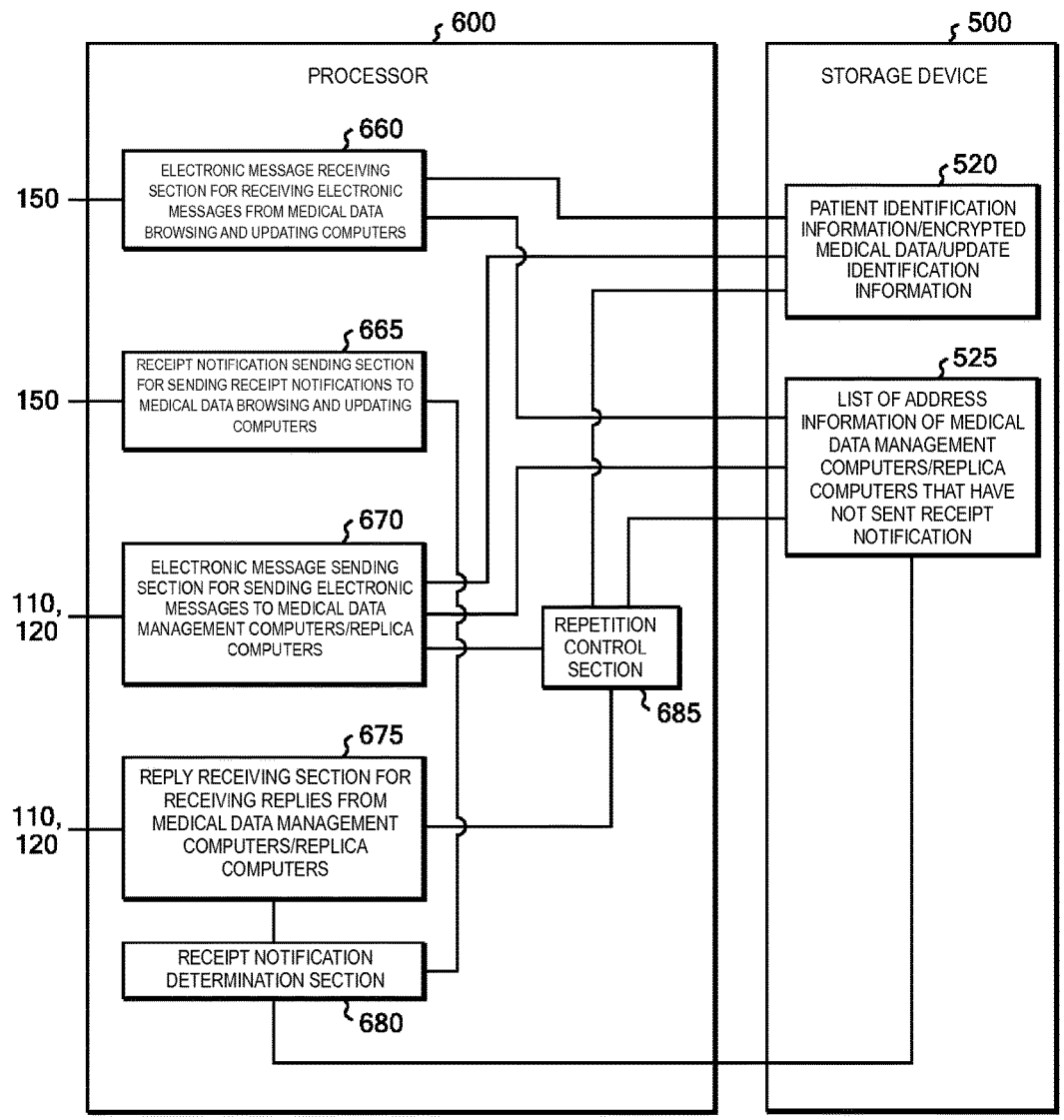
FIG. 8 is a schematic functional block diagram of a medical data temporary storage computer 140.

FIG. 8 illustrates a configuration used for implementing the functions of the processor 600 in a medical data temporary storage computer 140 to distribute and store medical data over wide area. The processor 600 includes an electronic message receiving section 660 for receiving medical messages from medical data browsing and updating computers, a receipt notification sending section 665 for sending receipt notifications to medical data browsing and updating computers, an electronic message sending section 670 for sending electronic messages to medical data management computers/replica computes, a reply receiving section 675 for receiving replies from medical data management computers/replica computers, a receipt notification determination section 680, and a repetition control section 685, all of which can be implemented by computer programs or micro codes. For this configuration of the processor 600, storage areas are provided in the storage device 500 for storing patient identification information/encrypted medical data/update identification information 520 and a list 525 of address information of medical data management computers/replica computers that have not sent receipt notifications.

The electronic message receiving section 660 for receiving electronic messages from medical data browsing and updating computers receives an electronic message 350 as illustrated in FIG. 4 that includes the identification information of the patient, the encrypted medical data, the associated update identification information, and the address information of medical data management computers 110 or medical data management replica computers 120 that have not sent a receipt notification. The electronic message receiving section 660 for receiving electronic messages from medical data browsing and updating computers places and stores the identification information of the patient, the encrypted medical data and the associated update identification information in the patient identification information/encrypted medical data/update identification information 520, which is a storage area in the storage device 500, and places and stores the address information of the medical data management computers 110 or medical data management replica computers 120 that have not sent a receipt notification on the list 525 of address information of medical data management computers/replica computers that have not sent a receipt notification, which is a storage area in the storage device 500.

The electronic message sending section 670 for sending electronic messages to medical data management computers/replica computers retrieves the address information of the medical data management computers 110 or medical data management replica computers 120 that have not sent a receipt notification from the list 525 of address information of medical data management computers/replica computers that have not sent a receipt notification, retrieves the patient identification information, the update identification information and the encrypted medical data from the patient identification information/encrypted medical data/update identification information 520 and sends an electronic message 300 as illustrated in FIG. 3 that include the patient identification information, the update identification information and the encrypted medical data to those medical data management computers 110 or medical data management replica computers 120 that have not sent a reception notification.

The reply receiving section 675 for receiving replies from medical data management computers/replica computers receives a reply from medical data management computers 110 or medical data management replica computers 120 to which the electronic message sending section 670 for sending electronic messages to medical data management computers/replica computes has sent the electronic message and provides the received replies to the receipt notification determination section 680. The reply receiving section 675 for receiving replies from medical data management computers/replica computers notifies the repetition control section 685 of the reception of the reply.

The receipt notification determination section 680 determines whether or not the reply from each medical data management computer 110 or medical data management replica computer 120 is a receipt notification. For example, the receipt notification determination section 680 is configured to compare information in the reply with information in a predetermined receipt notification to identify and determine whether the reply is a receipt notification. If the reply is a receipt notification, the receipt notification determination section 680 provides the address information of the medical data management computer 110 or the medical data management replica computer 120 that has sent the receipt notification to the receipt notification sending section 665 for sending receipt notifications to medical data browsing and updating computers. The receipt notification determination section 680 provides the address information of the computer to which the electronic message has been sent and from which a reply has been received to the list 525 of address information of medical data management computers/replica computers that have not sent receipt notifications regardless of whether the reply is a receipt notification or not so that the provided address information is deleted from the list 525 of address information.

The receipt notification sending section 665 for sending receipt notifications to medical data browsing and updating computers sends the address information, provided from the receipt notification determination section 680, of the medical data management computer 110 or medical data management replica computer 120 that has sent the receipt notification to the medical data browsing and updating computer 150 along with information indicating that the medical data management computer 110 or medical data management replica computer 120 has sent the receipt notification.

When the repetition control section 685 is notified by the reply receiving section 675 for receiving replies from medical data management computers/replica computers that the reply receiving section 675 has received a reply, the repetition control section 685 refers to the list 525 of address information of medical data management computers/replica computers that have not sent receipt notifications to determine whether or not there remains address information on the list 525. If address information remains on the address information list 525, the repetition control section 685 instructs the electronic message sending section 670 for sending electronic messages to medical data management computers/replica computers to repeat sending the electronic message. If no address information remains on the address information list 525, the repetition control section 685 instructs the storage device 500 to delete the encrypted medical data and the stored patient identification information, the encrypted medical information, and the associated update identification information are deleted from the patient identification information/encrypted medical data/update identification information 520.

Figure 9:
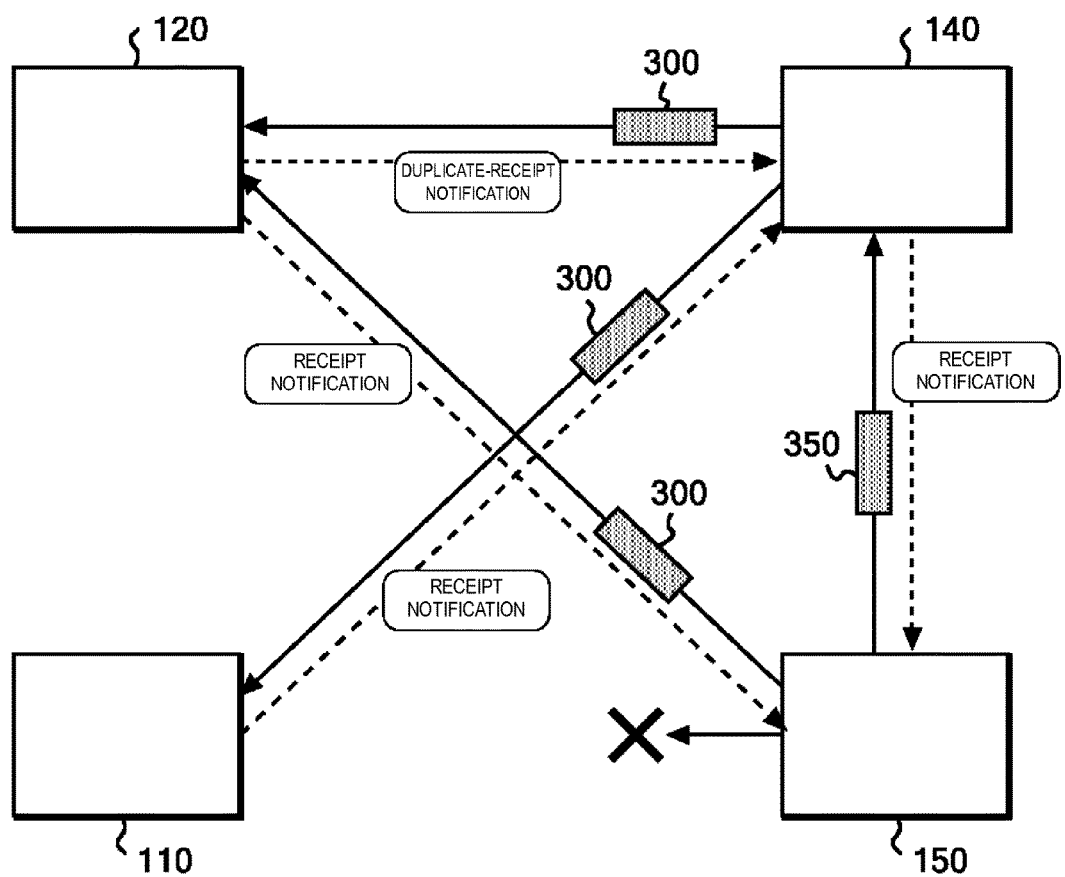
FIG. 9 is a diagram schematically illustrating a flow of data on a communication network during storing medical data.

FIG. 9 schematically illustrates a flow of data when medical data is distributed and stored over a wide area on a communication network. A medical data browsing and updating computer 150 sends an electronic message 300 including encrypted medical data of a patient as illustrated in FIG. 3 to a medical data management computer 110. Since the medical data management computer 110 is shut down, the transmission fails as indicated by the mark X. On the other hand, the medical data browsing and updating computer 150 also sends the electronic message 300 to medical data management replica computer 120. Since the medical data management replica computer 120 is in operation, the medical data management replica computer 120 successfully receives the electronic message 300 and then sends a receipt notification to the medical data browsing and updating computer 150. If the medical data browsing and updating computer 150 has not yet received a receipt notification from the medial data management replica computer 120, the medical data browsing and updating computer 150 sends an electronic message 350 including medical data of a patient as illustrated in FIG. 4 to a medical data temporary storage computer 140 in order to request the medical data temporary storage computer 140 to send the electronic message 300 to the medical data management replica computer 120 as well as the medical data management computer 110. The medical data temporary storage computer 140 sends the electronic message 300 to the medical data management computer 110, receives a receipt notification from the medical data management computer 110, and sends the receipt notification to the medical data browsing and updating computer 150. On the other hand, the medical data temporary storage computer 140 also sends the electronic message 300 to the medical data management replica computer 120. Since the medical data management replica computer 120 has already received the electronic message 300 from the medical data browsing and updating computer 150, the medical data management replica computer 120 sends a duplicate-receipt notification to the medical data temporary storage computer 140. The medical data temporary storage computer 140 receives the duplicate-receipt notification but does not send the duplicate-receipt notification to the medical data browsing and updating computer 150 because the duplicate-receipt notification is unnecessary.

From a practical point of view, however, sharing of electronic records has not been widespread. This is because building a system that manages electronic medical records costs a large amount of money. For example, the following "three criteria for electronic medical records" are required to be met for sharing electronic medical records.

1. Authenticity
   Intentional or accidental input of false data and intentional or accidental alteration, deletion, or confusion of data should be prevented.
   Where the responsibility for making medical records lies should be clarified.
2. Visual Readability
   Data should be readily made readable to the naked eye as needed.
   Data should be able to be immediately presented on paper as needed.
3. Storability
   Data should be stored for a legally-defined period of time in such a way that the data can be restored.

Meeting criteria 3 (Storability) requires building of a robust database, resulting in a high system cost. Consequently, only well-financed medical institutions have introduced electronic medical record systems.

Another problem is that patients' electronic medical records can be lost in the event of a disaster at medical institutions having electronic medical record system. To prepare for such a disaster, a replica of an electronic medical record database needs to be maintained in a remote location. However, most medical institutions are community-based institutions and it is difficult for such medical institutions to maintain a replica database in a location remote from the medical institutions.

Past teachings in the area of medical record storage include a medical cooperation system in which a center server connected with a plurality of terminal devices through a communication network so that they can exchange data with each other includes a server controller that mediates between a source terminal device and a target terminal device to enable smooth cooperation between them. While the medical cooperation system may act as a wide-area system that covers remote locations because data is exchanged through a communication network, the system requires a management server that centrally manages data, such as a center server that performs control with terminal devices over the entire medical cooperation system.

Thus, as described herein, one object of the present invention is to implement a "medical information network" that enables distributed management of medical information across various computers on a communication network, instead of a particular medical institution holding an expensive electronic medical records system and managing electronic medical records. Objects of the present invention include providing a method, system and computer program that build a data management mechanism for implementing such a "medical information network" for distributing and managing medical information on a communication network spread over a wide area.

A method for distributing and managing medical information on a communication network over a wide area according to one embodiment provided by the present invention includes the steps of acquiring encrypted medical information from one of a plurality of first computers, which are connected to the communication network, hold identical medical information, encrypt medical information, and send and receiving encrypted medical information, by a second computer connected to the communication network, decrypting the acquired encrypted medical information on the second computer, browsing and updating the decrypted medical information and encrypting the browsed and updated medical information on the second computer, and sending the encrypted browsed and updated medical information from the second computer to the plurality of first computers.

In one embodiment of the present invention, the step of acquiring includes the step of acquiring address information of a plurality of first computers from one or more third computers and sending a medical information request to first computers associated with the acquired address information, the one or more third computers being connected to the communication network and holding address information of the plurality of first computers.

In one embodiment of the present invention, the step of decrypting includes the step of acquiring decryption information for decrypting the acquired encrypted medical information from a user of a first computer and applying the decryption information to the decryption and the step of encrypting comprises the step of acquiring encryption information for encrypting browsed and updated medical information from the user of the first computer and applying the encryption information to the encryption.

In one embodiment of the present invention, the step of sending to a plurality of first computers includes the step of sending an electronic message including encrypted browsed and updated medical information and update identification information to the plurality of first computers and receiving a receipt notification.

In one embodiment of the present invention, the step of sending to a plurality of first computers includes the step of, if the number of first computers from which a receipt notification has been received after the first transmission of an electronic message is smaller than the number of first computers to which the electronic message has been sent at the first transmission, sending an electronic message including the encrypted browsed and updated medical information, update identification information and address information of a first computer that has not sent a receipt notification to one or more fourth computers, which are connected to the communication network, receive encrypted medical information, temporarily hold the encrypted medical information and send the encrypted information, and receiving a receipt notification from the first computer from the one or more fourth computers.

In one embodiment of the present invention, the step of sending to a plurality of first computers includes the step of, if the sum of the number of first computers from which a receipt notification has been directly received and the number of first computers from which a receipt notification has been received through a fourth computer is smaller than the number of first computers to which the electronic message has been sent at the first transmission, repeating the steps of sending the electronic message including the encrypted browsed and the updated medical information and update identification information to a first computer that has not sent a receipt notification and sending to the fourth computer the electronic message including the encrypted browsed and updated medical information, the update identification information and the address information of the first computer that has not sent a receipt notification, until the sum reaches the number of the first computers to which the electronic message has been sent at the first transmission.

In one embodiment of the present invention, the method further includes the steps of receiving, at a fourth computer, an electronic message including encrypted browsed and updated medical information, update identification information and address information of a first computer that has not sent a receipt notification, sending an electronic message including encrypted browsed and updated medical information and update identification information from the fourth computer to the first computer identified by the address information of the first computer that has not sent a receipt notification, and receiving a receipt notification from the first computer at the fourth computer and sending the receipt notification to a second computer.

In one embodiment of the present invention, the method further includes the steps of, when a receipt notification or a duplicate-receipt notification is received at a fourth computer from a first computer, deleting address information of the first computer that has sent the receipt notification or the duplicate-receipt notification from the address information of first computers that have not sent a receipt notification, and until the address information of first computers that have not sent a receipt notification becomes empty, repeating at the fourth computer the steps of sending the electronic message including the encrypted browsed and updated medical information and the update identification information from the fourth computer to the first computers identified by address information of the first computers that have not sent a receipt notification, and receiving a receipt notification from the first computer at the fourth computer and notifying the second computer of the reception.

In one embodiment of the method presented herein, the first computers are a medical data management computer and a medical data management replica computer, the second computer is a medical data browsing and updating computer, the third computer is a medical data address management computer, and the fourth computer is a medical data temporary storage computer.

A computer program for distributing and managing medical information on a communication network over a wide area according to one embodiment provided by the present invention causes a second computer to execute the steps of the method that are performed by the second computer and causes a fourth computer to execute the steps of the method that are performed by the fourth computer.

A system distributing and managing medical information on a communication network over a wide area according to one embodiment provided by the present invention includes a plurality of first computers connected to the communication network, the plurality of first computers holding identical medical information, encrypting the medical information and sending and receiving the encrypted medical information, and a second computer connected to the communication network, the second computer comprising an acquisition section for acquiring encrypted medical information from any of the plurality of first computers, a decrypting section for decrypting the encrypted medical information acquired by the acquisition section, a browsing and updating section for browsing and updating the medical information decrypted by the decrypting section, an encryption section for encrypting the medical information browsed and updated on the browsing and updating section, and a sending section for sending the browsed and updated medical information encrypted by the encryption section to the plurality of first computers.

In one embodiment of the present invention, the acquisition section includes an address information acquisition section acquiring address information of a plurality of first computers from one or more third computers and sends a medical information request to first computers associated with the acquired address information, the one or more third computers being connected to the communication network and holding address information of the plurality of first computers.

In one embodiment of the present invention, the decrypting section decrypts the acquired encrypted medical information with decryption information acquired from a user of a first computer and the encryption section encrypts the browsed and updated medical information with encryption information acquired from the user of the first computer.

In one embodiment of the present invention, the browsing and updating section generates update identification information indicating that medical information has been browsed and updated.

In one embodiment of the present invention, the sending section is provided with encrypted browsed and updated medical information and update identification information, generates an electronic message including the encrypted browsed and updated medical information and the update identification information, sends the electronic message to the plurality of first computers and, if the number of first computers from which a receipt notification has been received after the first transmission of the electronic message is smaller than the number of first computers to which the electronic message has been sent at the first transmission, sends an electronic message including the encrypted browsed and updated medical information, the update identification information and address information of a first computer that has not sent a receipt notification to one or more fourth computers, which are connected to the communication network, receive encrypted medical information, temporarily hold the encrypted medical information, and send the encrypted medical information.

In one embodiment of the present invention, if the sum of the number of first computers from which a receipt notification has been directly received and the number of first computers from which a receipt notification has been received through a fourth computer is smaller than the number of first computers to which the electronic message has been sent at the first transmission, the sending section repeats sending the electronic message including the encrypted browsed and updated medical information and the update identification information to a first computer that has not sent a receipt notification and sending to the fourth computer the electronic message including the encrypted browsed and updated medical information, the update identification information and the address information of a first computer that has not sent a receipt notification, until the sum reaches the number of the first computers to which the electronic message has been sent at the first transmission.

In one embodiment of the present invention, the fourth computer includes an electronic message receiving section receiving an electronic message including encrypted browsed and updated medical information, update identification information and address information of a first computer that has not sent a receipt notification, an electronic message sending section sending an electronic message including encrypted browsed and updated medical information and update identification information to a first computer identified by the address information of the first computer that has not sent a receipt notification, a notification receiving section receiving a receipt notification from the first computer, and a notification sending section sending the receipt notification from the first computer to a second computer.

In one embodiment of the present invention, when a fourth computer receives a receipt notification or a duplicate-receipt notification from a first computer, the fourth computer deletes address information of the first computer that has sent the receipt notification or the duplicate-receipt notification from the address information of the first computers that have not sent a receipt notification and, until the address information of first computers that have not sent a receipt notification becomes empty, repeats sending the electronic message including the encrypted browsed and updated medical information and the update identification information to the first computers identified by the address information of the first computers that have not sent a receipt notification, receiving a receipt notification from the first computer and notifying the second computer of the reception.

In one embodiment the presently described inventive system, the first computers are a medical data management computer and a medical data management replica computer, the second computer is a medical data browsing and updating computer, the third computer is a medical data address management computer, and the fourth computer is a medical data temporary storage computer.

Thus, the present invention implements a "medical information network" that enables distributed management of medical information across various computers on a communication network. In particular, one embodiment of the present invention provides a method, system and computer program that build a data management mechanism for implementing such a "medical information network" for distributing and managing medical information on a communication network over a wide area. According to the present invention, encrypted medical data can be reliably transferred and stored on a communication network and even a medical institution that does not have an expensive database system can ensure authenticity, visual readability and storability on a small system (for example, an application running on personal computers PC) to handle electronic medical records.

While the present invention has been described with an embodiment thereof, the technical scope of the present invention is not limited to the scope described with respect to the embodiment. Various modifications or improvements can be made to the embodiment and it will be understood that such modified or improved embodiment are included in the technical scope of the present invention.

What is claimed is:

1. A method comprising:
    acquiring, by a second computer and from a third computer, address information of a plurality of first computers, wherein the address information of the plurality of first computers is associated with patient medical information for a particular patient;
    storing, on the second computer, the address information of the plurality of first computers in an address list in the second computer;
    transmitting, by the second computer, updated medical information from the second computer to the plurality of first computers, wherein the updated medical information is stored in a persistent storage device in the second computer;
    receiving, by the second computer, receipt notifications from a portion of the plurality of first computers, wherein the receipt notifications acknowledge receipt of the updated medical information, and wherein only the portion of the plurality of first computers responded to the updated medical information from the second computer;
    in response to the portion of the plurality of first computers being less than all of the plurality of first computers, sending, from the second computer, directions to one or more fourth computers to reiteratively send the updated medical information until all of the plurality of first computers that did not send receipt notifications to the second computer send receipt notifications of the updated medical information to the one or more fourth computers, wherein the first computers and the one or more fourth computers are at a same location, and wherein the second computer is in a location that is remote from the plurality of first computers and the one or more fourth computers;
    receiving, by the second computer and from the one or more fourth computers, information from the one or more fourth computers indicating that all of the plurality of first computers that did not send receipt notifications to the second computer have sent receipt notifications to the one or more fourth computers indicating receipt of the updated medical information; and
    in response to receiving the information from the one or more fourth computers indicating that all of the plurality of first computers have sent receipt notifications to the one or more fourth computers indicating receipt of the updated medical information, deleting the addresses of the plurality of first computers that did send receipt notifications to the one or more fourth computers from the address list on the second computer and deleting the updated medical information from the persistent storage device in the second computer.

2. The method of claim 1, further comprising:
    determining, by the second computer, whether address information of a computer that holds medical information for a particular patient is held within the second computer; and
    acquiring, by the second computer and from the third computer, the address information of the plurality of first computers in response to determining that the second computer does not hold the medical information for the particular patient.

3. The method of claim 1, further comprising:
    configuring, by one or more processors, the third computer from a remote computer that is located in a remote location that is remote from a location of all of the plurality of first computers, wherein the remote location is not vulnerable to a disaster that would disable the plurality of first computers at locations of the plurality of first computers, and wherein said configuring configures the third computer with an ability to recreate the plurality of first computers; and
    in response to the disaster disabling the plurality of first computers, recreating, by the third computer, the plurality of first computers.

4. The method of claim 1, wherein the plurality of first computers are a medical data management computer and a medical data management replica computer, the second computer is a medical data browsing and updating computer, the third computer is a medical data address management computer, and the one or more fourth computers are medical data temporary storage computers.

5. The method of claim 1, wherein the one or more fourth computers contain a stored list of address information of the plurality of first computers that did not send receipt notifications to the second computer, and wherein the method further comprises:
    in response to the one or more fourth computers receiving the notice that all of the plurality of first computers have sent a receipt notification acknowledging receipt of the updated medical information, deleting, by the one or more fourth computers, the stored list of address information of the plurality of first computers that did not send receipt notifications to the second computer from the one or more fourth computers.

6. The method of claim 1, wherein the portion of the plurality of first computers that respond at a time that the second computer sent the updated medical information are computers that were turned on at the time that the second computer sent the updated medical information, and wherein computers from the plurality of first computers that did not respond at the time that the second computer sent the updated medical information are computers that were turned off at the time that the second computer sent the updated medical information.

7. The method of claim 1, wherein the one or more fourth computers contain a stored list of address information for the plurality of first computers that did not send receipt notifications to the second computer, and wherein the method further comprises:
    receiving, by the one or more fourth computers, a duplicate-receipt notification from a particular computer from the plurality of first computers that did not send receipt notifications to the second computer, wherein the duplicate-receipt notification indicates that the particular computer has already received the updated medical information from the second computer; and in response to receiving the duplicate-receipt notification, deleting, by the one or more fourth computers, the particular computer from the stored list of address information for the plurality of first computers that did not send receipt notifications to the second computer.

8. A computer program product comprising a non-transitory computer readable storage medium having program code embodied therewith, the program code readable and executable by a processor to perform a method comprising:
    transmitting, by a second computer, updated medical information from the second computer to a plurality of first computers, wherein the updated medical information is stored in the second computer;

receiving, by the second computer, receipt notifications from a portion of the plurality of first computers, wherein only the portion of the plurality of first computers responded to the updated medical information from the second computer;

in response to the portion of the plurality of first computers being less than all of the plurality of first computers, sending, by the second computer, directions to one or more fourth computers to reiteratively send the updated medical information until all of the plurality of first computers that did not send receipt notifications to the second computer send receipt notifications of the updated medical information;

receiving, by the second computer and from the one or more fourth computers, addresses of all of the plurality of first computers that did not send receipt notifications to the second computer but that did send receipt notifications to the one or more fourth computers; and in response to receiving the addresses of all of the plurality of first computers that did not send receipt notifications to the second computer but that did send receipt notifications to the one or more fourth computers, deleting the addresses of the plurality of first computers that did send receipt notifications to the one or more fourth computers from the address list on the second computer and deleting the updated medical information from the persistent storage device in the second computer.

9. The computer program product of claim 8, wherein the method further comprises:

acquiring decryption information for decrypting encrypted medical information from a user of one of the plurality of first computers and applying the decryption information to the encrypted medical information; and acquiring encryption information for encrypting updated medical information from the user of one of the plurality of first computers and applying the encryption information to encrypt the updated medical information.

10. The computer program product of claim 8, wherein the method further comprises:

configuring, by one or more processors, the third computer from a remote computer that is located in a remote location that is remote from a location of all of the plurality of first computers, wherein the remote location is not vulnerable to a disaster that would disable the plurality of first computers at locations of the plurality of first computers, and wherein said configuring configures the third computer with an ability to recreate the plurality of first computers; and in response to the disaster disabling the plurality of first computers, recreating, by the third computer, the plurality of first computers.

11. The computer program product of claim 8, wherein the method further comprises:

determining, by the second computer, a quantity of previously non-responsive first computers that have not acknowledged receipt of the updated medical information from the second computer; and establishing, by the second computer, a quantity of the fourth computers that exceeds the quantity of the previously non-responsive first computers.

12. The computer program product of claim 8, further comprising:

determining, by the second computer, whether address information of the plurality of first computers that hold medical information for the particular patient is held within the second computer;

in response to determining that the second computer does not hold the address information of the plurality of first computers that hold medical information for the particular patient, acquiring, by the second computer and from a third computer, the address information of the plurality of first computers, wherein the address information of the plurality of first computers is associated with patient identification information for the particular patient, wherein the plurality of first computers, the second computer, and the third computer are connected to the network.

13. A computer system comprising:

one or more processors;

one or more computer readable memories; and one or more non-transitory computer readable storage mediums, wherein program instructions are stored on at least one of the one or more non-transitory computer readable storage mediums for execution by at least one of the one or more processors via at least one of the one or more computer readable memories to perform a method comprising:

acquiring, from a third computer, address information of a plurality of first computers, wherein the address information of the plurality of first computers is associated with patient medical information for a particular patient;

storing the address information of the plurality of first computers in an address list in the computer system;

transmitting updated medical information to the plurality of first computers, wherein the updated medical information is stored in a persistent storage device in the computer system, and wherein the plurality of first computers are physically located at a service provider that provides medical data management services;

receiving receipt notifications from a portion of the plurality of first computers, wherein the receipt notifications acknowledge receipt of the updated medical information, wherein only the portion of the plurality of first computers responded to the updated medical information from the computer system;

in response to the portion of the plurality of first computers being less than all of the plurality of first computers, sending directions to one or more fourth computers to reiteratively send the updated medical information until all of the plurality of first computers that did not send receipt notifications to the computer system send receipt notifications of the updated medical information to the one or more fourth computers;

receiving, from the one or more fourth computers, addresses of all of the plurality of first computers that did not send receipt notifications to the computer system but that did send receipt notifications to the one or more fourth computers; and in response to receiving the addresses of all of the plurality of first computers that did not send receipt notifications to the computer system but that did send receipt notifications to the one or more fourth computers, deleting the addresses of the plurality of first computers that did send receipt notifications to the one or more fourth computers from the address list on the computer system and deleting the updated medical information from the persistent storage device in the computer system.

* * * * *